Figure 1:
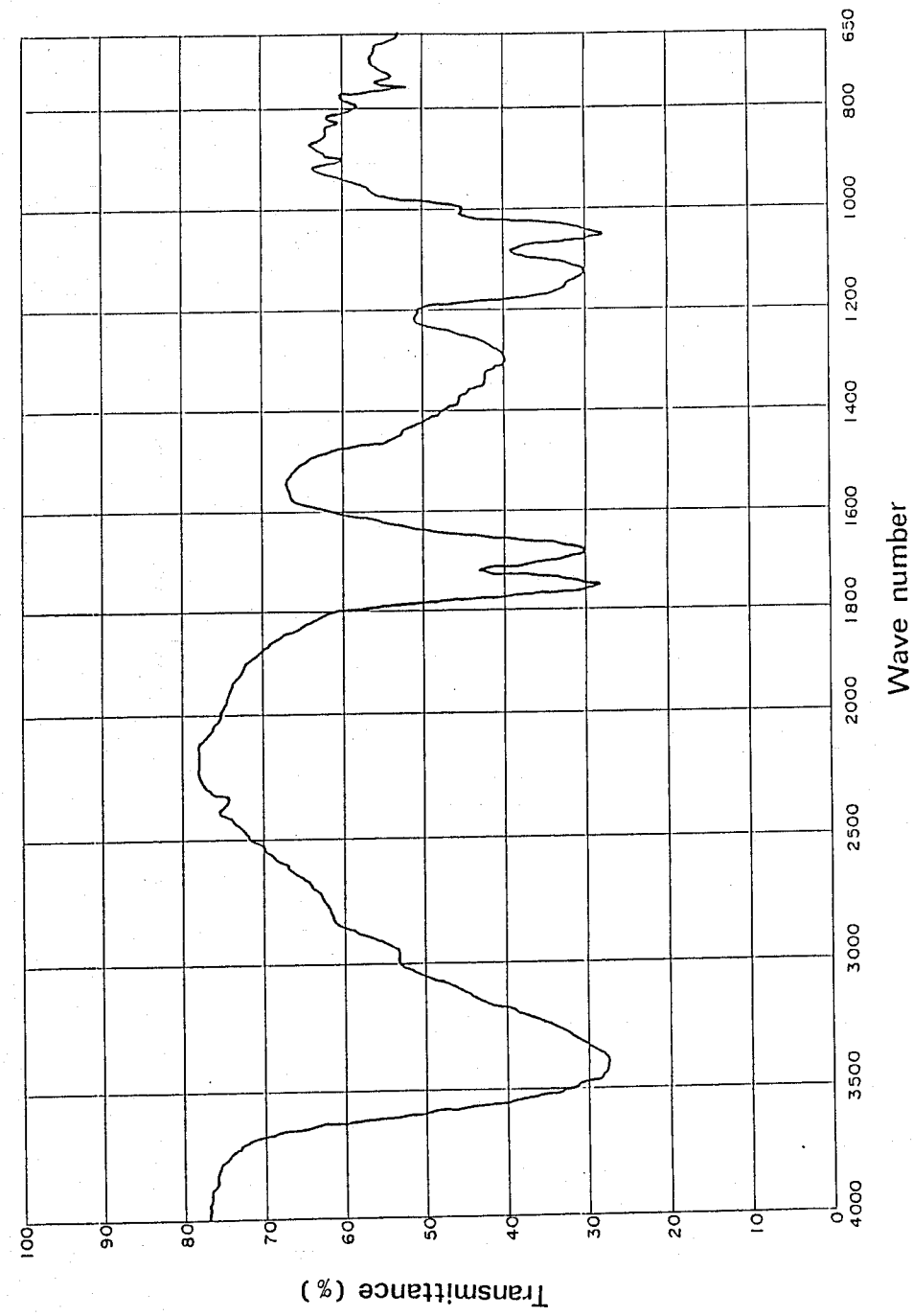

United States Patent [19]

Takanohashi et al.

[11] Patent Number: 4,845,246

[45] Date of Patent: Jul. 4, 1989

[54] ASCORBIC ACID ESTER

[75] Inventors: Kunio Takanohashi, Kawanishi; Mitsutaka Tanaka, Sanda; Toru Yamano, Itami, all of Japan

[73] Assignee: Takeda Chemical Industries, Ltd., Osaka, Japan

[21] Appl. No.: 205,094

[22] Filed: Jun. 10, 1988

[30] Foreign Application Priority Data

Jun. 15, 1987 [JP] Japan .................. 62-148374

[51] Int. Cl.$^4$ ............................. C07D 307/62
[52] U.S. Cl. ........................................ 549/315
[58] Field of Search ............................ 549/315

[56] References Cited

U.S. PATENT DOCUMENTS 2,185,383 1/1940 Pasternack et al. ............... 260/344

FOREIGN PATENT DOCUMENTS 0000092 2/1978 European Pat. Off. .
48-15931 5/1973 Japan .
WO87/00839 2/1987 PCT Int'l Appl. .

OTHER PUBLICATIONS

Ahmedabad, Chemical Abstracts, vol. 97, No. 9, Aug. 30, 1982, p. 671, No. 72714m.
Khacaturov et al., Chemical Abstracts, vol. 94, No. 8 (Feb. 23, 1981) p. 364 No. 52833j.
Koen et al., Chemical Abstracts, vol. 96, No. 22, Jun. 8, 1987, p. 428, No. 187386C.
Basnak et al., Chemical Abstracts, vol. 106, No. 23, Jun. 8, 1987, p. 777, No. 196736U.

*Primary Examiner*—Glennon H. Hollrah
*Assistant Examiner*—Mark W. Russell
*Attorney, Agent, or Firm*—Wenderoth, Lind & Ponack

[57] ABSTRACT

6-O-(2-keto-L-gulonoyl)-L-ascorbate substantially free from 2-keto-L-gulonic acid is produced by allowing an acid to act on 2-keto-L-gulonic acid in an inert organic solvent and recovering 6-O-(2-keto-L-gulonoyl)-L-ascorbate from the reaction mixture.

6-O-(2-keto-L-gulonoyl)-L-ascorbate is more fat-soluble than L-ascorbic acid and is expected of the use as a prodrug for L-ascorbic acid that can be absorbed from the intestinal tract.

1 Claim, 4 Drawing Sheets

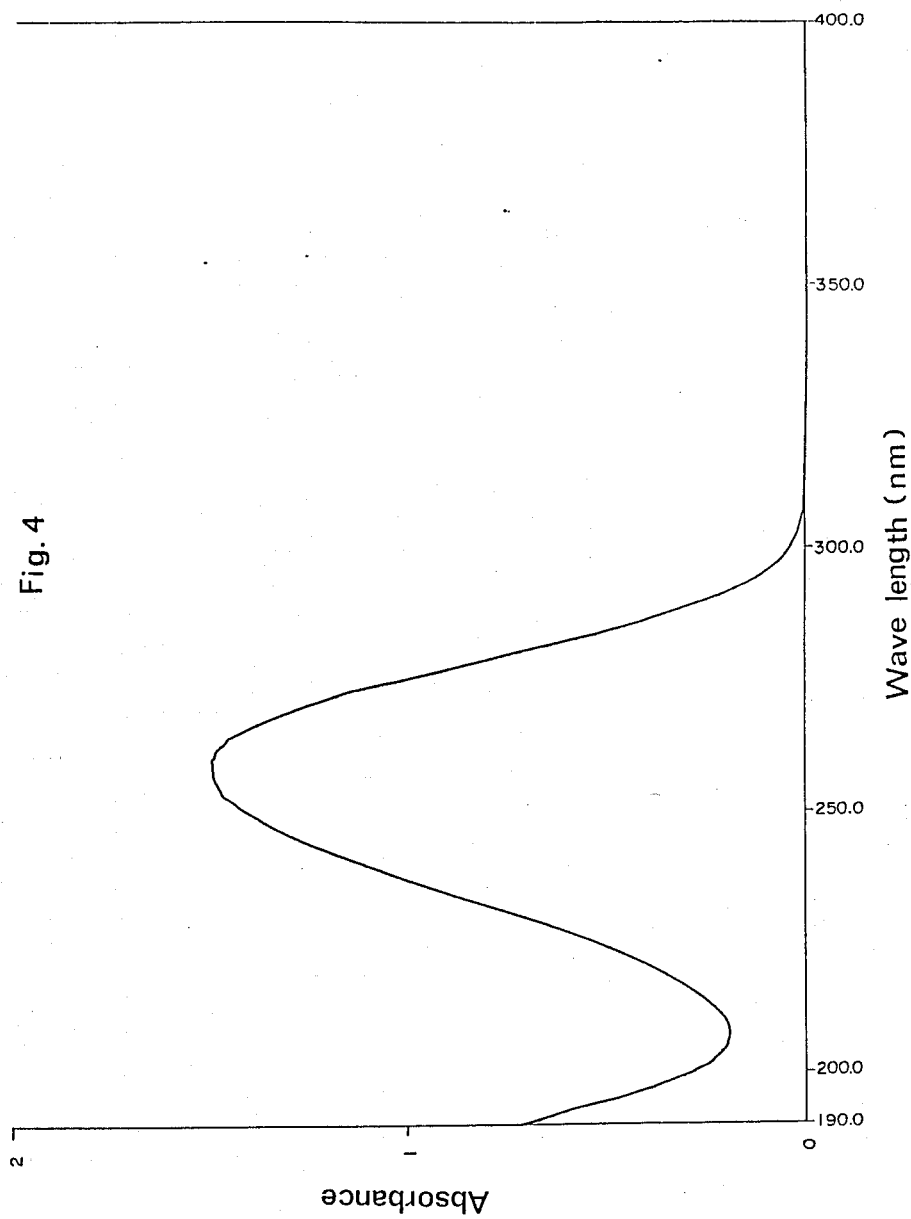

ASCORBIC ACID ESTER

This invention relates to a novel L-ascorbic acid ester and a method of producing the ester.

There has been known a method of producing L-ascorbic acid in which 2-keto-L-gulonic acid or its mono- or diacetone derivative is used as the starting material [For example, U.S. Pat. No. 2,185,383 (1940), Japanese Exam. Pat. Pub. 48-15931 (1973), PCT WO 87/00839 (1987)]. The inventors have found that a novel compound is produced in the reaction mixture of the known method. The inventors succeeded in isolation of the new compound from the reaction mixture in the form substantially free from the starting material. It was also found that one mole of the novel compound produces 2 moles of L-ascorbic acid when the compound was treated with a base. The present invention is based on these findings.

Thus, this invention is directed to (1) 6-O-(2-keto-L-gulonoyl)-L-ascorbate substantially free from 2-keto-L-gulonic acid, and (2) a method of producing 6-O-(2-keto-L-gulonoyl)-L-ascorbate free from 2-keto-L-gulonic acid, which comprises allowing an acid to act on 2-keto-L-gulonic acid or its ketal in an inert organic solvent until 6-O-(2-keto-L-gulonoyl)-L-ascorbate is substantially produced in the reaction mixture and isolating 6-O-(2-keto-L-gulonoyl)-L-ascorbate therefrom.

The reaction of 2-keto-L-gulonic acid or its ketal for producing the ester is carried out in the presence of a mineral acid such as hydrochloric acid in an inert organic solvent such as aromatic hydrocarbons (e.g. benzene, toluene) at from room temperature to 70° C., preferably 60°-70° C. The procedures to increase the yield of the ester include use of a small amount (about 0.1 to 2 weight % of the starting material) of an acid and existence of a small amount of water in the reaction mixture (0.5 to 5 weight % of the amount of the starting material).

Isolation of the novel compound 6-O-(2-keto-L-gulonoyl)-L-ascorbate substantially free from 2-keto-L-gulonic acid from the reaction mixture is performed by using an adsorbent. Such adsorbents include synthetic porous resin such as Amberlite XAD-II (manufactured by Organo Co.). Isolation of 6-O-(2-keto-L-gulonoyl)-L-ascorbate using such an adsorbent is performed as follow: the reaction mixture is added to water, and the aqueous layer after kept standing is separated. The aqueous layer is then allowed to pass through a column packed with Amberlite XAD-II, and the desired 6-O-(2-keto-L-gulonoyl)-L-ascorbate is eluted with water. 6-O-(2-keto-L-gulonoyl)-L-ascorbate can be isolated and recovered, because the unreacted starting material 2-keto-L-gulonic acid is eluted with water faster than the ester. The eluates are combined and concentrated to dryness or freeze-dried, to give 6-O-(2-keto-L-gulonoyl)-L-ascorbate substantially free from 2-keto-L-gulonic acid.

Silica gel also can be used as the adsorbent for isolating 6-O-(2-keto-L-gulonoyl)-L-ascorbate from the reaction mixture. With this adsorbent, 6-O-(2-keto-L-gulonoyl)-L-ascorbate can be isolated in the form substantially free from 2-keto-L-gulonic acid and L-ascorbic acid: namely, the residue obtained by concentration to dryness of the reaction mixture is dissolved in a mixture of acetone and benzene (about 1:1 v/v), the resultant solution is allowed to flow through a column packed with silica gel, and the desired compound is eluted with a mixture of acetone and benzene.

The fractions containing 6-O-(2-keto-L-gulonoyl)-L-ascorbate are combined and concentrated to give the 6-O-(2-keto-L-gulonoyl)-L-ascorbate in the form substantially free from 2-keto-L-gulonic acid and L-ascorbic acid.

The 6-O-(2-keto-L-gulonoyl)-L-ascorbate substantially free from 2-keto-L-gulonic acid obtained by the above methods can be purified, for example, by the use of the adsorbents described above.

The result of the elemental analysis of the ester obtained in Example 1 is:

Elemental analysis for $C_{12}H_{16}O_{12} \cdot H_2O$: Calc. C: 38.93, H, 4.90, Found C: 38.77, H, 4.84.

Figure 2:
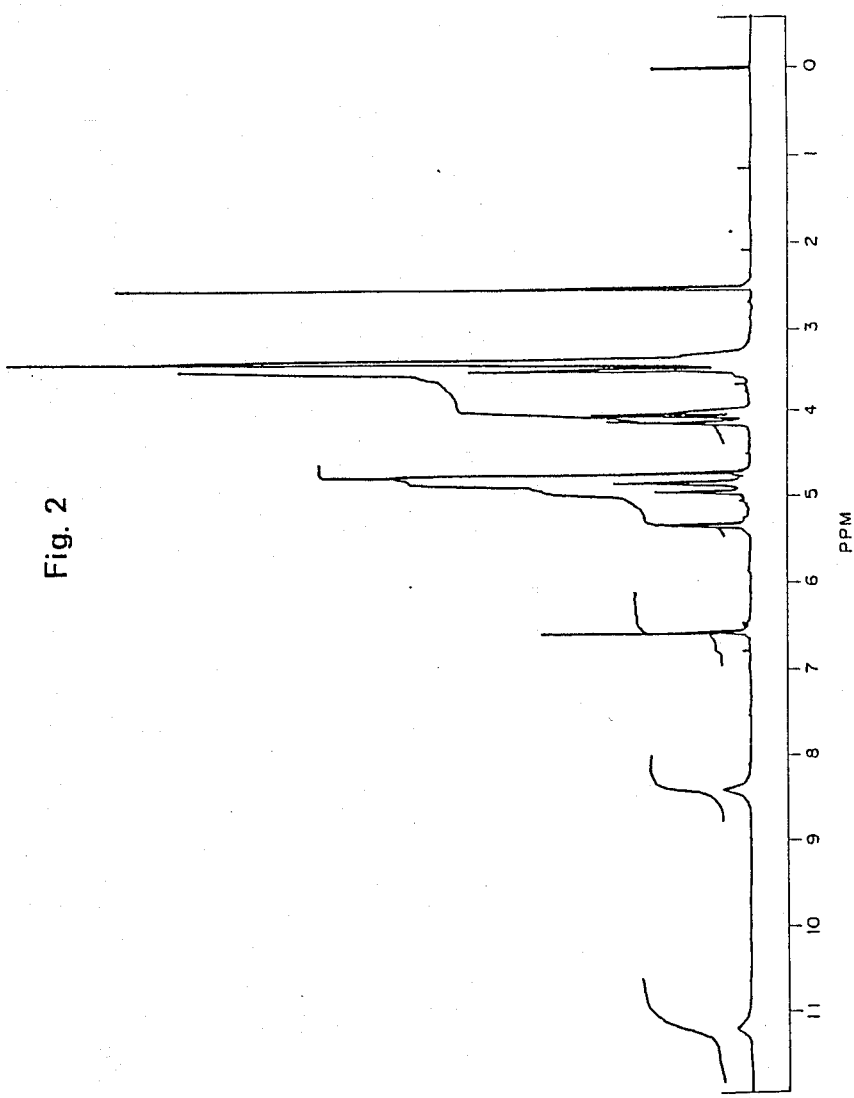
Figure 3:
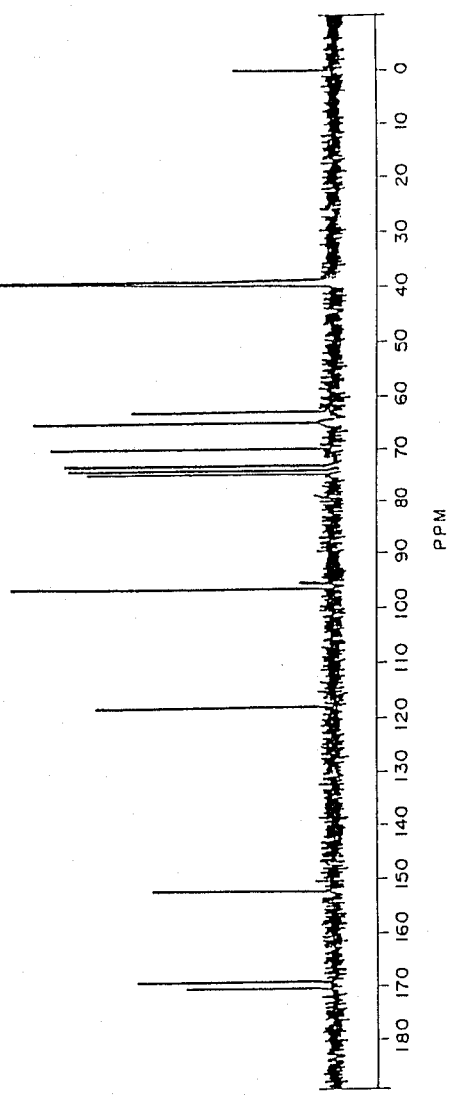

The IR absorption spectrum, $^1$H-NMR spectrum, $^{13}$C-NMR spectrum, and UV absorption spectrum of the ester are shown in FIGS. 1–4, respectively.

Based on the results of elemental analysis, various spectrochemical analyses and mass spectrometry, the ester isolated in Example 1 was identified to be 6-O-(2-keto-L-gulonoyl)-L-ascorbate.

6-O-(2-keto-L-gulonoyl)-L-ascorbate substantially free from 2-keto-L-gulonic acid of this invention can produce L-ascorbic acid on hydrolysis.

Such hydrolysis can be performed by treatment with a basic substance, particularly a weakly basic substance, such as sodium hydrogencarbonate and potassium hydrogen-carbonate in water or a hydrous organic solvent (lower alcohols such as methanol, ethanol, propanol; ketones such as acetone, methyl ethyl ketone; nitriles such as acetonitrile, propionitrile). The amount of the basic substances to be used is normally 1–10 mol., preferably 1–7 mol. The reaction temperature is 20°–70° C., preferably 25°–60° C. and the reaction time is normally 1–6 hours.

For production of L-ascorbic acid from an ester of 2-keto-L-gulonic acid, such as a methyl ester, the reaction is carried out with a strongly basic substance such as sodium hydroxide and sodium methylate in a substantially anhydrous solvent. However, the hydrolysis of the ester of the present invention and the ring-closing reaction proceed substantially with a weakly basic substance in water or a hydrous solvent and 2 moles of the L-ascorbic acid is produced from one mole of the starting compound. The novel ester of this invention can produce L-ascorbic acid even in the Solution B of Disintegration Test (pH 6.8) described in Japanese Pharmacopia XI.

6-O-(2-keto-L-gulonoyl)-L-ascorbate substantially free from 2-keto-L-gulonic acid of this invention, due to its ester bond in the molecule, is more fat-soluble than L-ascorbic acid and is hydrolyzed and lactonized easily even in the Solution B of Disintegration Test in JP XI to give 2 moles of the L-ascorbic acid; thus it is expected of the use as a prodrug for L-ascorbic acid that can be absorbed from the intestinal tract. The administration route and dosage of the ester can be similarly usable to those of L-ascorbic acid. In addition 6-O-(2-keto-L-gulonoyl)-L-ascorbate substantially free from 2-keto-L-gulonic acid of this invention produces L-ascorbic acid of high quality in a high yield under mild conditions.

In the following the invention is illustrated in more concrete with Examples.

EXAMPLE 1

Diacetone-2-keto-L-gulonic acid monohydrate, 20 g (68.5 mmol), was added to 60 ml of toluene and stirred at 40° C. To this was added 1 ml of 35% hydrochloric acid and stirred for 5 hours. After completion of the reaction, the solvent was evaporated off under reduced pressure. The residue was dissolved in 80 ml of a mixture of acetone and benzene (1:1 v/v). The solution was allowed to pass through a column packed with 600 ml of silica gel (4 cm in diameter×50 cm) at SV=0.5. Elution was made at SV=1–1.5 with 1.2 l of the 1:5 (v/v) mixture, and 1.2 l of the 1:1 (v/v) mixture, and 3 l of the 5:1 (v/v) mixture of acetone and benzene. The fractions eluted with the 5:1 (v/v) mixture of acetone and benzene were combined and concentrated to dryness under reduced pressure. The residue was dissolved in 50 ml of water, and allowed to pass through a column of 1.5 l of Amberlite XAD-II. Elution was made with water. The fractions containing 6-O-(2-keto-L-gulonoyl)-L-ascorbate were combined, and freeze-dried. 6-O-(2-keto-L-gulonoyl)-L-ascorbate substantially free from 2-keto-L-gulonic acid, 14.5 g, was obtained (yield: 60%).

$^1$H-NMR (400 MHz, DMSO-d$_6$): δ: 11.19 (s, 1H), 8.41 (s, 1H), 6.58 (s, 1H), 5.34 (d, 1H, J=5.9 Hz), 4.96 (d, 1H, J=5 Hz), 4.86 (d, 1H, J=3 Hz), 4.74 (d, 1H, J=1.7 Hz), 4.16 (dd, 1H, J=6.7 Hz, 10.4 Hz), 4.06 (dd, 1H, J=7.0 Hz, 10.4 Hz).

$^{13}$C-NMR (400 MHz, DMSO-d$_6$): δ: 170.24 (s), 169.03 (s), 151.13 (s), 118.07 (s), 96.39 (s), 74.52 (d), 73.65 (d), 72.68 (d), 69.79 (s), 64.95 (d), 64.95 (d), 64.95 (t), 62.85 (t).

IR (KBr disk): ν max (cm$^{-1}$) 3370, 1760, 1700, 1690, 1280, 1040.

UV (H$_2$O) λ max (ε): 260 (9300).

Mass (SIMS) M/e: 352.

The IR absorption spectrum chart, $^1$H-NMR spectrum chart, $^{13}$C-NMR spectrum chart, and UV absorption spectrum chart of the 6-O-(2-keto-L-gulonoyl)-L-ascorbate substantially free from 2-keto-L-gulonic acid obtained in this Example are shown in FIGS. 1–4, respectively.

EXAMPLE 2

2-keto-L-gulonic acid, 20 g (purity: 99.5%, 103 mmol), and 90 mg of stearylpropylenediamine dioleate were added to 90 ml of toluene, and stirred at 65° C. To this was added 1.5 ml of concentrated hydrochloric acid. Further treatment was the same as in Example 1. The amount of 6-O-(2-keto-L-gulonoyl)-L-ascorbate substantially free from 2-keto-L-gulonic acid obtained was 15.6 g (43%).

REFERENCE EXAMPLE 1

6-O-(2-keto-L-gulonoyl)-L-ascorbate substantially free from 2-keto-L-gulonic acid, 1.2 g (3.4 mmol), was dissolved in 50 ml of water, to which 1.4 g (17 mmol) of sodium hydrogencarbonate was added and stirred at 40° C. for about 1.5 hours. High performance liquid chromatography analysis of the reaction mixture showed that 1.14 g (yield: 95.2%) of L-ascorbic acid was present with 0.07 g of 2-keto-L-gulonic acid but the starting substance 6-O-(2-keto-L-gulonoyl)-L-ascorbate was not found. Condition of high performance liquid chromatography:

Column: HPX-87H manufactured by Bio Rad Co.
Mobile phase: 0.1M ammonium sulfate.
Detection: differential refractometer.

REFERENCE EXAMPLE 2

6-O-(2-keto-L-gulonoyl)-L-ascorbate substantially free from 2-keto-L-gulonic acid, 1.2 g (3.4 mmol), was dissolved in 50 ml of water, to which a solution of 1.8 g (8.5 mmol) of sodium carbonate in 5 ml of water was added and stirred at 40° C. for about 2 hours. Quantitative analysis of the reaction mixture according to the method described in Reference Example 1 showed that 1.10 g (yield: 91.9%) of L-ascorbic acid was present with 0.05 g of 2-keto-L-gulonic acid.

REFERENCE EXAMPLE 3

6-O-(2-keto-L-gulonoyl)-L-ascorbate substantially free from 2-keto-L-gulonic acid, 141 mg, was dissolved in 100 ml of Solution B of Disintegration Test in JP XI (6.804 g of monobasic potassium phosphate is dissolved in 23.6 ml of 1N sodium hydroxide, to which water is added to make 1 l. pH=6.78), and stirred at 37° C. The reaction mixture was analyzed by high performance liquid chromatography and the following results were obtained.

| Reaction time (hour) | yield (wt %) |
| --- | --- |
| 2 | 77 |
| 4 | 84 |

We claim:
1. 6-O-(2-keto-L-gulonoyl)-L-ascorbate substantially free from 2-keto-L-gulonic acid.

* * * * *